United States Patent
Tulleken et al.

[11] Patent Number: 5,964,750
[45] Date of Patent: Oct. 12, 1999

[54] LASER CATHETER FOR BYPASS SURGERY

[75] Inventors: Cornelis A F Tulleken, Naarden; Rudolf M. Verdaasdonk, Houten; Hendricus Jacobus Mansvelt-Beck, Bilthoven, all of Netherlands

[73] Assignee: Medolas Gesellschaft fuer Medizintechnik GmbH, Germany

[21] Appl. No.: 09/016,311

[22] Filed: Jan. 30, 1998

Related U.S. Application Data

[62] Division of application No. 08/704,716, Sep. 16, 1996.

[51] Int. Cl.$^6$ .................................................. A61B 17/36
[52] U.S. Cl. .................................................. 606/15; 606/7
[58] Field of Search ................................... 606/7, 13–16; 607/88, 89, 92

[56] References Cited

U.S. PATENT DOCUMENTS

| | | |
|---|---|---|
| 3,805,793 | 4/1974 | Wright . |
| 4,913,142 | 4/1990 | Kittrell et al. ............................... 606/7 |
| 4,993,412 | 2/1991 | Murphy-Chutorian ....................... 606/7 |
| 5,188,632 | 2/1993 | Goldenberg ................................. 606/7 |
| 5,281,213 | 1/1994 | Milder ........................................ 606/15 |

FOREIGN PATENT DOCUMENTS

| | | |
|---|---|---|
| 0 141 536 | 10/1984 | European Pat. Off. . |
| WO 87/04611 | 8/1987 | WIPO . |
| WO 88/04157 | 6/1988 | WIPO . |
| WO 91/01690 | 2/1991 | WIPO . |
| WO 91/05332 | 4/1991 | WIPO . |

*Primary Examiner*—Beverly M. Flanagan
*Assistant Examiner*—Roy Gibson
*Attorney, Agent, or Firm*—Evenson, McKeown, Edwards & Lenahan P.L.L.C.

[57] ABSTRACT

The invention provides a laser catheter for pinpointed application of laser light on the walls of intracorporal vessels, having a ring-shaped arrangement of optical fibers which surround a central longitudinal channel. A stop element at the distal region of the laser catheter widens the outer circumference, through which the optical fibers pass in beam direction. At the distal catheter tip, the fibers form a planar, ring-shaped light, exit area. The longitudinal channel of the laser catheter is provided at its distal end with a perforated member which is disposed at a short distance from the plane, ring-shaped light exit area in a direction opposite the beam direction. A second element is provided which is attached to a vessel wall as a spacer and engages, during the laser light application procedure with the element widening the circumference of the light catheter.

6 Claims, 5 Drawing Sheets

LASER CATHETER FOR BYPASS SURGERY

This application is a division of application Ser. No. 08/704,716, filed Sep. 16, 1996.

BACKGROUND AND SUMMARY OF THE INVENTION

The present invention relates to a laser catheter for pinpointed application of laser light on the walls of intracorporal vessels, the laser catheter having optical fibers which are disposed ring-shaped and surround an inner hollow channel.

There are increasing possible uses of laser catheters in surgery due to the growing number of different structural designs of laser catheters and their distal end regions.

For instance, laser catheter tips are known which can, in particular, be employed in bypass surgery and which are especially distinguished by the fact that the cross section of the distal end of the laser catheter at which the light exits is completely composed of optical fibers. Such catheters are referred to, by way of illustration, as "full multifiber catheters".

With the aid of the aforementioned type of catheter, techniques for laser-aided anastomosis (surgical joining of two hollow organs, such as, attaching an additional blood-carrying channel (bypass) to a bloodchannel artery whose flow cross section is narrowed by deposits) are known, which permit bypass surgery without interrupting the blood flow in the main artery. For instance, the essays published by Rudolf Verdaasdonk et al. ("End-to-Side Anastomosis of Small Vessels Using an Nd:YAG Laser with a Hemispherical Contact Probe"; J. Neurosurg Vol. 76, March 1992; "Use of the Excimer Laser in HighFlow Bypass Surgery of the Brain", J. Neurosurg, Vol. 78, March 1993) deal with a surgical technique presenting bypass surgery in the brain with the aid of neodym-YAG or excimer lasers, without impairing the blood flow of the main blood-carrying artery affected by the surgery.

First a bypass is sewn onto the outer circumference of the artery to be treated. Through this bypass, a laser catheter tip, which is designed elastically at the distal end, is inserted and positioned within the bypass, onto the outer wall of the main artery to be treated. The laser is activated and by means of an ablation process makes a hole in the main artery (through which a part of the blood flow can be diverted) in the region of the light exit at the distal end of the optical fiber.

In addition to the great advantage of being able to conduct bypass surgery without interrupting the main artery, which is especially vital in bypass surgery in the brain, however, this known surgical technique has the drawback that the ablated material from the vessel wall resulting from-the light impingement by the laser catheter tip remains inside the blood stream and, under unfavorable circumstances may reach points in the blood stream of smaller diameter and obstruct them totally. In particular, in the brain, such tiny particles of tissue in the blood stream circulation are the cause of spontaneous strokes.

The described bypass surgery technique and the optical fiber arrangement therefor for the distal end regions of catheters, are discussed in a publication of the Medical Laser Center, Heart-Lung Institute, Department of Neurosurgery entitled "Multifiber Excimer Laser Catheter Design Strategies for Various Medical Applications" by R. Verdaasdonk et al.

The object of the present invention is to design a laser catheter for pinpointed application of laser light at the walls of intracorporal vessels, such laser catheter having optical fibers which are ring-shaped and surround an inner hollow channel, in such a manner that the risk of ablation remains obstructing blood-carrying vessels following the application of laser light is completely eliminated.

Another object of the invention is to provide a laser catheter arrangement such that the separation of the vessel wall to be treated corresponds exactly to the geometry of the tip of the laser catheter in order to permit a predefined cross section for the vessel wall penetration.

These and other objects and advantages are achieved by the present invention, which is based on the one hand on a special design of the tip of the laser catheter that makes it possible for the first time to make a geometrically exactly predefined hole in the wall of a vessel to be treated, and at the same time ensures that separated remains of the vessel wall do not stay in the blood stream, but rather are brought out of the body with the aid of the laser catheter.

For this purpose, the laser catheter according to the invention has optical fibers which are disposed in a ring-shaped configuration surrounding an inner hollow channel, and is provided at the outer circumference of its distal end with a circumference-widening element through which the optical fibers penetrate in the beam direction. With this arrangement of the optical fibers, the distal tip of the laser catheter thus assumes the form of a planar, ring-shaped light exit area.

The element widening the outer circumference of the laser catheter serves basically as a type of stop device which permits the surgeon to determine when the ring-shaped optical fibers projecting at its distal end have reached the maximal penetration depth through the region of the vessel wall which is to be ablated. The surgeon must terminate the penetration procedure at the latest when the edge of the outer circumference of the widening elements comes into contact with the outer wall of the vessel itself or with an object joined to the outer wall of the vessel. By the stop edge coming into contact with the outer wall of the vessel, the outer wall of the vessel is pressed into the same shape as the design of the stop edge, ensuring that the optical fibers rest evenly on the vessel wall.

Furthermore, the ring-shaped arrangement of the optical fibers permits separation of a circular disk of the wall vessel which is deposited inside the optical fiber arrangement. If the laser catheter is carefully extracted from the cut vessel wall, no ablation remains stay in the blood circulation system, because the circular, separated piece of vessel wall is held inside the laser catheter, by means of the low pressure prevailing therein.

The invented laser catheter is also provided with a perforated member disposed at its distal end terminating the hollow channel. The distance from the perforated member to the planar, ring-shaped light exit area of the optical fibers corresponds at least to the thickness of the to be ablated vessel wall. With such dimensioning, the elastic vessel wall is sucked to the top side of the perforated member by the low pressure prevailing inside the hollow channel, in an advantageous manner. Consequently, on the one hand, the light exit area of the optical fibers comes fully into contact with the surrounding vessel wall and, on the other hand, the vessel wall lies largely very close to the inner profile yielded by the ring-shaped optical fiber channel and the perforated member in order to ensure circular separation of the vessel wall.

Furthermore, according to the present invention, the separation procedure can be optimized by the catheter tip's engaging, during application of the laser light, with a particularly disposed ring-shaped element, on the one hand ensuring that the separation of the piece of the vessel wall occurs completely and on the other hand preventing any further injury to vessel walls, (such as to the opposite vessel wall of the blood-carrying artery). The ring-shaped element is joined to the bypass channel independent of the catheter tip in such a manner that the vessel wall is made taut during application of the laser light. Thus, the ring-shaped laser catheter tip rests evenly on the vessel wall, which is a prerequisite for a homogeneous light impingement.

The laser catheter tip according to the invention thus permits for the first time the achievement, from exterior of a vessel wall, of a controlled penetration through the vessel wall, without creating possible burnt waste products which may occur when the laser light is applied at the vessel wall, or other small pieces of vessel wall which can form for other reasons during cutting of the vessel wall. Consequently, the risk potential of blockage at distant bottlenecks in the blood stream due to burnt waste products is completely eliminated.

In an especially advantageous embodiment, if the hollow channel, which is surrounded by the ring-shaped optical fibers and is joined to a low pressure source, is provided at its distal end with a perforated member having an arrangement of concentrically disposed boreholes therein. Such boreholes perforate the member in such a manner that an even suction effect can be achieved in order to fix the separated vessel wall evenly to the surface of the perforated member, by means of the low pressure.

Other objects, advantages and novel features of the present invention will become apparent from the following detailed description of the invention when considered in conjunction with the accompanying drawings.

DETAILED DESCRIPTION OF THE DRAWINGS

Figure 1A:
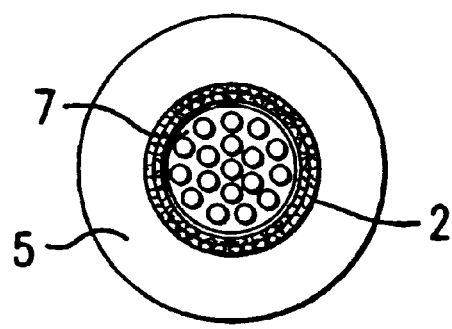
FIGS. 1a and 1b show respective top and front cross sectional views of an embodiment of the laser catheter tip according to the invention.
Figure 1B:
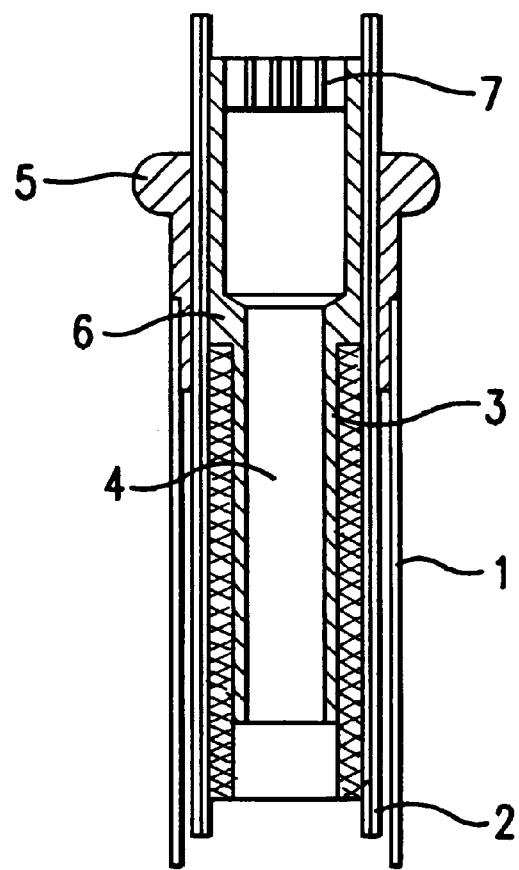
Figure 2:
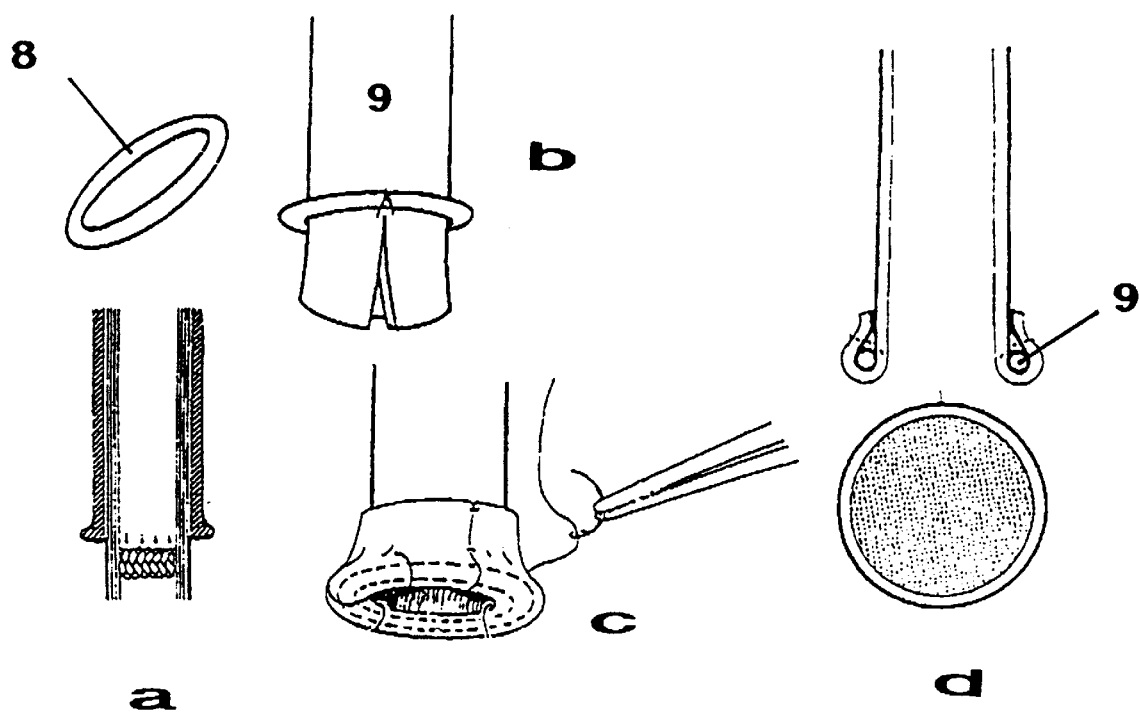
FIGS. 2a, b, c, d show preliminary measures for carrying out bypass surgery using the laser catheter tip according to the invention.
Figure 3:
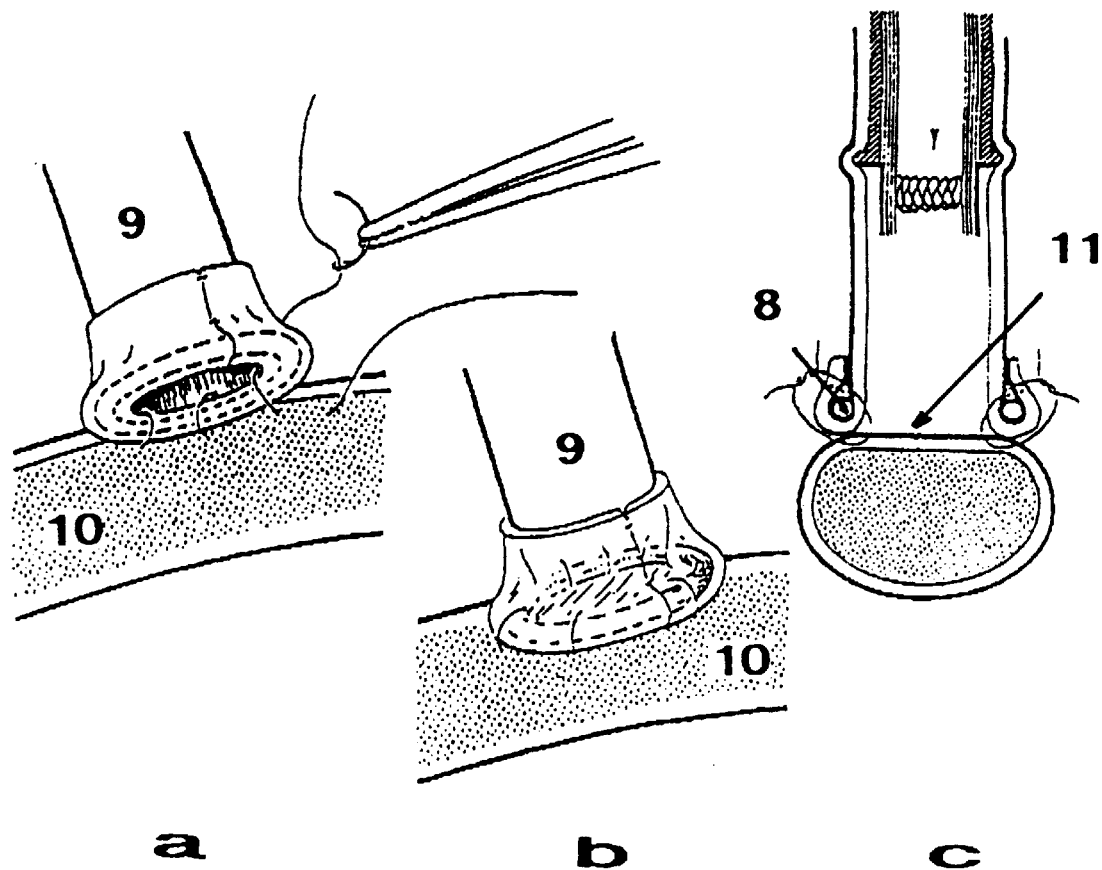
FIG. 3a, b, c is a schematic representation of various steps in attaching the bypass to a vessel wall to be treated.
Figure 4:
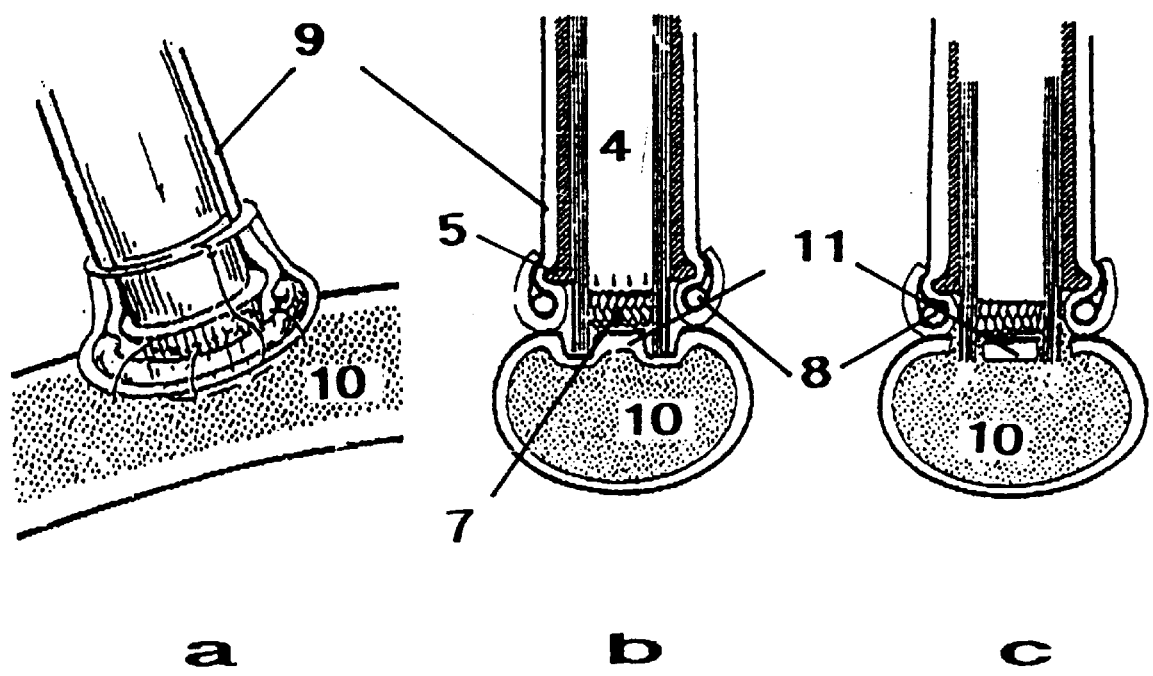
FIGS. 4a, b, c illustrate the manner of function of the laser catheter tip according to the invention during light application.
Figure 5:
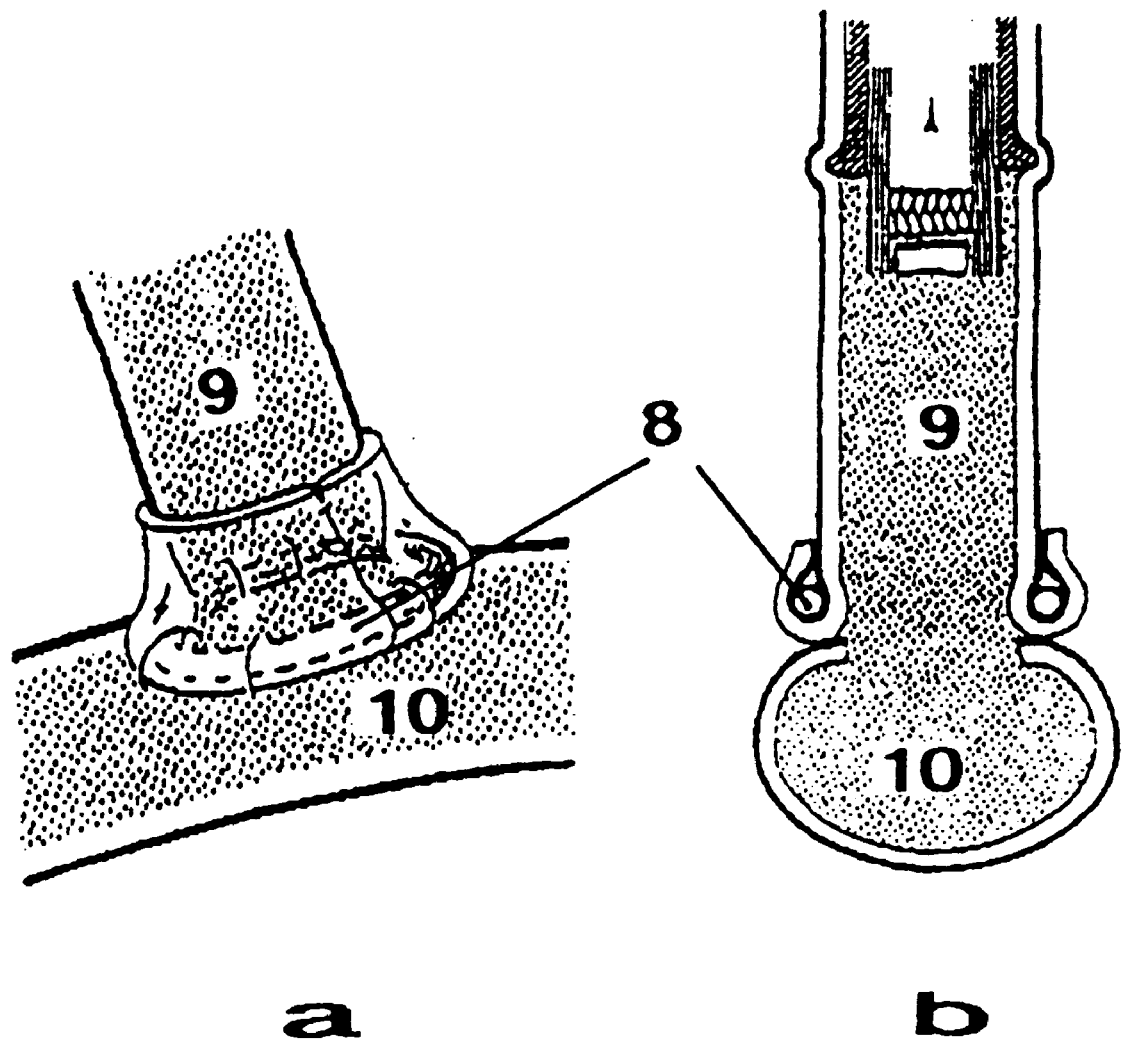
FIGS. 5a, b show the removal of the separated vessel wall by means of the laser catheter.

FIGS. 1.A and B show top and front cross sectional representations of the distal region of the laser catheter according to the invention. The laser catheter is surrounded by a casing 1, which meets the typical demands for use in the medical field, such as easy sterilization, high flexibility and material compatibility. The outer casing 1 surrounds the ring-shaped arrangement of the optical fibers 2 which are disposed in two layers, in two concentric circles in the preferred embodiment shown in FIG. 1.B. This can also be seen in the top view of the tip of the laser catheter of FIG. 1.A. In connection with an inner tube-shaped casing 3, a hollow channel 4 is surrounded, which is joined at its proximal end to a low pressure source (not shown in FIG. 1). At the tip of the distal region of the invented laser catheter, there is provided an outer circumference-widening element 5, which in the preferred embodiment has an atraumatic ring-shaped cross section, with a straight stop edge in the direction of the distal end. The dimensioning of the outer-circumference widening element 5 must be such that the outer circumference of the element widening the outer circumference of the laser catheter has at least the diameter of the vessel channel through which the laser catheter is to be guided. In this way, it is ensured that the catheter tip is centered inside the vessel channel in a self-guiding manner by resting with its circumference on the inside area of the vessel channel.

In the direction of the distal end of the laser catheter tip, the ring-shaped optical fibers 2 project beyond the plane of the widening element 5. The optical fibers 2 for their part surround a holding means 6, which represents on the proximal end a termination for the inner casing 3 but which, in particular provides, a holding device for a perforated member 7 which leads the low pressure prevailing inside the hollow channel 4 to the top side of the lid 7. A top view of the laser catheter tip in FIG. 1.A shows an advantageous arrangement of perforation boreholes, which are disposed in concentric circles. The top view representation also shows the circumference area of the element 5 widening the outer circumference of the laser catheter The typical dimensions of the laser catheter are scaled as follows: the outer diameter of the casing 1 of the laser catheter is 2.2 mm, whereas the diameter at the distal end region increases by means of element 5 to 3 mm. The optical fibers usually project 1.5 mm out of element 5 and have an outer diameter of 1.9 mm. At a distance of about 0.5 mm from the light exit area, the perforated member 7 is set inside the optical fibers 2. In the form depicted in FIG. 1, the perforated member 7 is provided with eighteen boreholes each having a diameter of 0.2 mm. However, the described sizes have to be adapted to the size conditions given by the dimensions of the vessel.

For a closer description of the manner of working of the laser catheter tip according to the invention, FIGS. 2 to 5 illustrate schematically the manner of applying it to carry out bypass surgery without interrupting the blood flow within the blood-carrying vessel.

FIG. 2a shows the laser catheter tip designed according to the present invention above which a ring-shaped element 8 is shown, the diameter of which is larger than the outer diameter of the ring-shaped disposed optical fibers and smaller than (or the same size as) the diameter of the element 5 widening the outer circumference of the laser catheter. Usually the inner diameter of the ring (made, for example, of a body-compatible platinum-irridium alloy) is 2.8 mm.

In preparation for the conduct of bypass surgery, the ring is slipped over a bypass vessel 9, which is taken from a different region of the body of the patient so that the surgical joining of such removed vessel, (such as a piece of artery) as a bypass for the blood-carrying vessel, is not complicated or prevented by the body's own rejection.

According to FIG. 2b, subsequently an incision is made into the removed artery, which is then wrapped upward about ring 9 and sewn around the latter, in the manner shown in FIG. 2c and 2d. In this way, a stable end of the vessel is obtained which according to FIG. 2d assumes the outer contour of ring 9 in a stable form.

Next, the vessel 9, thus prepared, is joined to the outer surface of the vessel channel 10 to be treated, by means of a ring-shaped seam, as shown in FIG. 3a. In the state according to FIG. 3b, the bypass vessel 9 rests firmly on the surface of the vessel 10 which is to be treated. Then the invented laser catheter is guided through the inside of the vessel channel 9 in direction of the vessel wall 11 of the vessel 10, a portion of which is to be severed. As FIG. 3c shows, the vessel region 11 is made taut for attaching the bypass, due to the ring 8 in such a manner that the distal end of the laser catheter can be placed on a plane area. This has the advantage that during laser light application, the vessel wall 11 is impinged evenly with laser light in the contact region with the light exit area. In this way, even material ablation at the vessel wall 11 is ensured.

FIG. 4a shows a perspective representation of the connection of the vessels 9 and 10 as well as the entry of the laser catheter tip through the vessel 9. The laser catheter tip is, as depicted in FIG. 4b, first guided through vessel 9 until the light exit area of the distal laser catheter tip rests on the vessel wall 11 to be separated. Thereafter, the low pressure source connected to the hollow channel 4 is activated and ensures that the separated piece of vessel wall 11 is drawn to the surface of the perforated member 7.

Now the laser light source is activated (in the present application, preferably an excimer laser for generating ultraviolet radiation). The laser is operated in pulses with a repetition frequency of 40 Hz, for about 5 seconds, so that about 200 pulses with an energy of 15 mJ impinge upon the tissue. The laser catheter tip thus slowly penetrates the lumen of the vessel 10 until the stop edge of the element 5 widening the outer circumference of the laser catheter touches the vessel wall which is pressed inside by ring 8. Thus as shown in FIG. 4c, the piece of the vessel wall 11 is separated from the remaining wall of the vessel 10, and adheres to the surface of the perforated member 7.

According to FIGS. 5a and b, the blood can now flow through the vessel channel 9 after the distal end of the laser catheter has been removed from the bypass vessel channel 9, together with the separated piece of vessel wall 11. The platinum irridium ring 8 remains continuously at the bypass connection between the vessel channels 9 and 10.

By means of the invention, it is for the first time possible to conduct bypass surgery without interrupting the blood flow in the blood vessels to be treated. Such interruptions particularly in the brain, can be a major risk to patients. With the aid of the invented laser catheter tip to be used in conjunction with the invented ring-shaped device, precise penetration of the vessel walls can be made without leaving remains of the vessel walls in the blood stream, which might obstruct narrow sites in the blood stream. Without further limitation of any possible applications of the described catheter tips in the field of medicine, the device can be utilized with any intracorporal vessels, in particular, for bypass surgery in the coronary vessels of the heart.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. A method of performing bypass surgery on intracorporal vessels comprising the steps of:

providing a laser catheter having a centrally disposed longitudinal optical fiber arrangement for delivering laser light from an end thereof, said catheter having a tip with a stop element widening an outer circumference thereof, said end of said optical fibers extending through said stop element in a beam travel direction;

attaching a rigid spacer element to an end of a bypass vessel;

attaching said end of said bypass vessel to an outer surface of a wall of a vessel which is to be treated;

inserting said catheter into said bypass vessel until said stop element abuts said spacer element;

applying laser light by means of said optical fiber, to ablate a portion of said wall of said vessel which is to be treated, whereby blood from said vessel to be treated can flow through said bypass vessel.

2. Method according to claim 1, wherein said spacer element is a ring.

3. Method according to claim 2, wherein said attaching step comprises:

placing said ring over said bypass vessel;

folding an end portion of said bypass vessel back on itself over said ring; and sewing said end portion to retain said ring, forming a rigid end of said bypass vessel.

4. Method according to claim 1, wherein said optical fiber arrangement has a central lumen which opens at said end of said optical fiber arrangement and which extends through said stop element, and wherein said method further comprises the step of:

applying a suction source to said lumen, whereby an ablated portion of said vessel wall is sucked and held against said end of said optical fiber arrangement which extends through said stop element.

5. Method according to claim 4, wherein said central lumen has a perforated member arranged at an open end thereof.

6. Method according to claim 5, wherein said perforated member has a plurality of longitudinal bore holes therethrough.

* * * * *